United States Patent [19]

Diggs

[11] Patent Number: 5,452,584
[45] Date of Patent: Sep. 26, 1995

[54] METHOD OF FREEZING BIOLOGICAL TISSUE SPECIMENS WITH OPTI-CRYO-FLUID

[75] Inventor: Juanita Diggs, Hillsborough, N.C.

[73] Assignee: Duke University, Durham, N.C.

[21] Appl. No.: 274,992

[22] Filed: Jul. 13, 1994

[51] Int. Cl.$^6$ .............................. F25D 17/02; F24F 3/16
[52] U.S. Cl. ................................ 62/64; 62/78; 62/51.1
[58] Field of Search ................................ 62/64, 78, 51.1

[56] References Cited

U.S. PATENT DOCUMENTS

| | | | |
|---|---|---|---|
| 4,489,569 | 12/1984 | Sitte | 62/51.1 X |
| 4,730,460 | 3/1988 | Coelho et al. | 62/64 |
| 4,799,361 | 1/1989 | Linner | 62/64 |
| 4,865,871 | 9/1989 | Livesay et al. | 62/64 X |
| 5,167,451 | 12/1992 | Müller et al. | 374/45 |
| 5,289,689 | 3/1994 | Cornwell et al. | 62/64 |

OTHER PUBLICATIONS

Elias, Jules M. "Developments in Immunohistochemistry and Enzyme Histochemistry", *Principles and Techniques in Diagnostic Histopathology* (1990).
3M Industrial Chemical Products Division, "Advanced Vapor Degreasing" (Dec., 1992).
3M Industrial Chemical Products Division "Liquid Burn–In Testing With Fluorinert™" (Apr., 1993).
Material Data Sheet (Jun., 1989) Eastman Kodak.
Material Safety Data Sheet (Apr., 1991) 3M Industrial Chemical Products Division.
Sales Brochure "Typical Property Comparisons for 3M Performance Fluids" (Nov., 1992).
Sales Brochure "PF–5060, A No Ozone–Depleting Alternative to CFCS" from 3M Industrial Chemical Products Division (Nov., 1992).
Sales Brochure "Improve the Quality of Frozen Sections with a Neslab Tissue Freezing Bath" from Neslab (1994).
"Microtomy & Cryotomy, Shandon–Lipshaw, Histobath™" (1994).
"Microcentrifuge Tube Handling & Storage" from USA/Scientific Plastics (1992).

*Primary Examiner*—Christopher Kilner
*Attorney, Agent, or Firm*—Richard E. Jenkins

[57] ABSTRACT

Disclosed is an improved method for freezing biological specimens, such as human tissues, animal tissues, and plant tissues. The specimens are frozen so that they may be presently examined with light microscopy, or first stored frozen at ultra low temperatures and then later examined with light microscopy. The specimens are prepared with a matrix gel and then frozen with a fluorinated carbon fluid that is non-toxic to humans and thus the method does not present adverse health effects to humans. Preferably, the fluid also is non-flammable. More preferably, the fluid also has an ozone depletion potential of 0, whereby the preferred procedure is free of detrimental effects on the protective ozone layer of the earth. A suitable fluorinated carbon fluid is one that stays in the liquid state at low temperatures, for instance −60° C. or lower. A suitable material is the perfluorinated carbon fluid, $C_6F_{14}$.

11 Claims, No Drawings

METHOD OF FREEZING BIOLOGICAL TISSUE SPECIMENS WITH OPTI-CRYO-FLUID

TECHNICAL FIELD

The present invention relates, in general, to a method for freezing biological specimens, such as human tissues, non-human animal tissues and/or plant tissues, so that they may be used for diagnosis by a pathologist and/or scientific investigator. Such specimens that are going to be frozen, as well as the frozen specimens, are referred to as "cryotomy tissues". For instance, human lymph node tissue having a suspect lesion may be frozen, sectioned, and stained, and then examined by a pathologist using light microscopy to determine if there are any cancer cells present therein. More particularly, the present invention relates to an improved method of freezing biological specimens with a fluorocarbon fluid that is non-toxic to the personnel working with it, and more preferably also is non-flammable and most preferably also does not deplete the protective ozone layer of the earth.

RELATED ART

Cryotomy tissues have long been used for surgical pathology diagnosis and/or for research purposes. Usually, a human surgical patient is the source of the tissue specimen, a typical human surgical specimen being about 2 cm in diameter. In that event, then within about 15 minutes or less, the specimen will be frozen and then diagnosed by a pathologist, while the patient is on the operating table under anesthesia and with the surgeon awaiting the diagnosis before continuing the surgery. As new regulations proposed by the College of American Pathologists will decrease the 15 minute turn around time to 5 to 8 minutes, it is important that the fluid employed in the freezing procedure freeze the specimen quickly.

A general overview of the current procedures for the freezing of specimens can be seen in Jules M. Elias, *Principles and Techniques in Diagnostic Histopathology*, Nayes Publications, Park Ridge, N.J. (1982). At page 20 of this book is described freezing a specimen with isopentane, the fluid most commonly used for freezing, and at page 180 of this book is a microphotograph of a frozen specimen.

More specifically, biological specimens, i.e., tissue samples, that are going to be frozen so that they may be examined by light microscopy are prepared as follows. First, the sample or specimen is removed from a biological subject. After removal, the specimen is placed within a mold that has been filled with a suitable matrix for cryotomy, a suitable matrix being optimum cutting temperature (hereinafter, abbreviated as OCT) gel, so that a coating of the matrix surrounds the specimen. The resultant assembly of mold with coated specimen therein is submerged in an appropriate fluid that, prior to submergence of the mold with coated specimen therein, has been placed in a receptacle (i.e., a flask or beaker) and pre-chilled, usually below −60° C.

The pre-chilling may be accomplished by surrounding the sides and bottom of the beaker containing the fluid with a freezing bath of liquid nitrogen or dry ice at the desired low temperature. As a container to hold the liquid nitrogen or dry ice, a foamed polystyrene cryo-transport box may be used, but also a commercially available recirculating freezing unit, i.e., an ultra low temperature freezer (a freezer that maintains a temperature of −60° C. or lower), may be employed for surrounding the beaker of fluid to pre-chill it.

The frozen mold with frozen specimen therein is then taken out of the fluid and sectioned while frozen in a cryostat maintained at a cold temperature. Hacker Instruments, Inc., of Fairfield, N.J., for instance, is a commercial supplier of cryostats.

The cryostat is a machine with a refrigerated cabinet that contains a microtome. The microtome makes slices through frozen tissue in micrometer-size increments, with the thickness of a typical slice being 5 micrometers. The cold temperature at which the cryostat is maintained during sectioning will vary depending on the kind of tissue being sectioned. For example, decalcified bone is sectioned at about −10° C. liver tissue at about −15° C. and breast tissue at about −30° C. After sectioning, each slice is mounted on a slide and stained with an appropriate dye therefor in order to be viewed under a microscope, for instance a light microscope, for diagnosis. Alternatively, if diagnosis is for a scientific investigation, for instance immunohistochemistry, rather than for a surgeon awaiting a quick answer in order to continue surgery on an anesthetized patient, the frozen mold with frozen specimen therein may be stored in an ultra low temperature freezer, and later, sectioned, mounted, stained, and examined.

About 40 years ago, scientists discovered that if the freezing were performed slowly, then large ice crystals would form in the interior of the specimen. More specifically, a specimen can be frozen by submerging it directly in liquid nitrogen, instead of placing it in a beaker of fluid and then placing the beaker in a liquid nitrogen bath. With large tissue specimens of about 2 to 4 cm in size, the liquid nitrogen causes a gas phase to form on the surface of the specimen, which in turn prevents heat from dissipating from the interior of the specimen, whereby the freezing proceeds too slowly. Then, large ice crystals form, disrupt cell membranes, and destroy or distort anatomical structures. This interference with morphology makes diagnosis of the frozen specimen difficult. Thus, direct freezing in liquid nitrogen is suitable only for very small specimens of about 1 mm in size, as these small specimens allow for the freezing to proceed rapidly.

A procedure that then developed to obviate the large ice crystal problem is to freeze the specimen rapidly in a transitional fluid at ultra low temperatures. This rapid freezing is colloquially referred to as "snap freezing" or "freeze quenching". Depending on the particular fluid employed (some fluids will stay liquid at a temperature lower than other fluids will), the ultra low temperature will range from −60° C. to −160° C. The fluids found to be appropriate for rapid freezing at ultra low temperatures are extremely volatile, and common examples of such fluids are isopentane (also known as 2-methyl butane), hexane, acetone, and dichlorodifluoromethane. However, each of these 4 fluids has its drawbacks.

As is well known, isopentane, hexane, and acetone are neurological, respiratory, and hepatic toxins to humans. Since they are toxic to humans, they present a danger of adverse health effects to any nearby persons who inhale them, especially those persons performing the freezing of the specimen.

Also, isopentane, hexane, and acetone are flammable and thus present, a danger of fire/explosion. In particular, isopentane, the most commonly used fluid as mentioned above, is denser than air and can easily move some distance from the beaker in which the freezing procedure is being performed. Thus, if the isopentane reaches a source of ignition, for instance an arcing motor or an open flame, it will ignite or explode.

Additionally, as noted above, dichlorodifluoromethane may be employed as the fluid for freezing of samples. Dichlorodifluoromethane is sold under the trademark FREON 12. (FREON® is a registered trademark of E.I. DuPont de Nemours and Company of Wilmington, Del., for various fluorinated carbon materials, for instance, $CFCl_3$, $CF_2Cl_2$, $CClF_3$, $CHF_3$, $CCl_2F$–$CClF_2$, and $CF_3$–$CF_3$, known as FREON 11, FREON 12, FREON 13, FREON 23, FREON 113, and FREON 116, respectively.) Personnel, who while working with FREON 12 inadvertently inhaled it, have reported palpitations and/or cardiac arrhythmia, and thus FREON 12 can be toxic and result in some adverse health effects to humans.

Moreover, as can be seen, FREON 12 is a chlorofluorocarbon (hereinafter, abbreviated as CFC). If a CFC is employed as the fluid for freezing, a hazard arises in that CFCs are detrimental to the protective ozone layer of the earth. More particularly, CFCs have been designated as having an ozone depletion potential (hereinafter, abbreviated as ODP) above 0, some having an ODP as high as 1. Specifically, FREON 12 has an ODP=1. As a result, the United States Government has imposed regulations requiring the phase-out of several CFCs for all but certain uses that are critical to the preservation of human life. Thus, finding suitable substitute fluids for freezing specimens, wherein the fluids have an ODP= 0, would be beneficial to the preservation of the earth's ozone layer.

It is noted that it is also known to freeze the assembly of the mold containing the coated specimen by placing it directly in the cryostat chamber. However, the drawback is that the cryostat is at a temperature from about $-10°$ C. to about $-30°$ C. whereas a desirable temperature, as noted above, is usually below about $-60°$ C.

Hence, it is desirable to find a hazard-free method of freezing biological specimens with a fluid that not only will be suitable at extremely low temperatures of about $-60°$ C. and below, but also will be non-toxic to humans, unlike such prior art fluids as isopentane, hexane, acetone, and dichlorodifluoromethane. Moreover, it is preferable that the fluid also be non-flammable to avoid the explosion/fire danger of isopentane, hexane, and acetone. Most preferably, the fluid will have an ODP=0, and thus not deplete the earth's ozone layer as dichlorodifluoromethane does.

SUMMARY OF THE INVENTION

Accordingly, the present invention provides a hazard-free method of freezing biological specimens to prepare them for examination by light microscopy. The examination may be performed presently or the frozen specimens may be placed in frozen storage and later examined by light microscopy.

The method comprises removing a biological specimen from a biological subject, such as a human, an animal, and/or a plant. Then, the method comprises coating the specimen with a matrix by placing the specimen within a mold containing the matrix, whereby an assembly of mold with coated specimen therein is formed.

Following coating, the method then comprises submerging the assembly in a pre-cooled fluorinated carbon fluid contained in a receptacle for a sufficient time to freeze the assembly. The fluid is suitable for freezing specimens at temperatures of about $-60°$ C. or lower and is pre-cooled to a temperature of about $-60°$ C. or lower. By "suitable" is meant that the fluid stays liquid at the low temperatures and does not also become frozen. Next, the method comprises removing the frozen assembly of frozen mold with frozen coated specimen therein from the fluid.

Lastly, the method further comprises that the freezing of the assembly of the mold with the coated specimen therein is accomplished with a fluorinated carbon fluid that is non-toxic to humans, whereby the method is free of adverse health effects to humans.

The method may further include that the frozen assembly having the frozen coated specimen therein, after removal from the fluid, is sliced into sections in a cryostat. Then, one or more of the sections are mounted on a slide or slides and stained with an appropriate dye therefor to reveal anatomical details of the specimen section when viewed with light microscopy, followed by examining the section with a light microscope.

Alternatively, the frozen assembly having the frozen coated specimen therein, after removal from the fluid, may be first stored in a cold atmosphere, such as in an ultra low freezer at an appropriate low temperature, and then later sliced into sections in a cryostat, one or more of the sections mounted on a slide or slides and stained, and then examined with a light microscope. Also alternatively, the mounted sections, either with or without first staining, may be stored in a cold atmosphere, such as in an ultra low freezer at an appropriate low temperature, and then later examined with a light microscope.

Thus, it is an object of the present invention to provide a method for freezing biological specimens that employs a fluid that is non-toxic to humans, thereby obviating the danger of adverse health effects to personnel, i.e. the person performing the freezing procedure, and/or to nearby persons.

Also, it is another object of the present invention that the frozen biological specimens may be either immediately examined by a pathologist, or stored and then later examined by a scientific investigator.

It is an advantage of the present invention that the morphology of specimens frozen via the method of the present invention is comparable to, i.e., substantially the same as, and often superior to, that of specimens frozen via prior art methods that use fluids hazardous to personnel and/or to the earth's ozone layer or use the inferior higher temperatures of the cryostat chamber itself.

It is a further advantage of the present invention that with the ultra low temperature of about $-60°$ C. or lower, the freezing time is short enough so that the freezing is rapid, whereby the frozen specimens are free of large ice crystals that distort anatomical structures and make diagnosis of the morphology of the frozen specimen difficult.

Some of the objects and advantages of the invention having been stated above, other objects, as well as other advantages, will become evident as the description proceeds, when taken in conjunction with the laboratory examples as best described below.

DETAILED DESCRIPTION OF THE INVENTION

Prior to discussing the laboratory examples, the following is noted with regard to the inventive method.

As can be seen by direct viewing via a light microscope, the inventive method produces frozen specimens in which the specimen integrity is maintained. In other words, the specimens have a resultant morphology which is comparable to, i.e., substantially the same as, and often superior to, that of specimens frozen via prior art methods that use fluids hazardous to personnel and/or to the earth's ozone layer or use the inferior higher temperatures of the cryostat chamber itself. Thus, the resultant morphology is the true morphology. Of course, this resultant morphology also can be seen from viewing micro-photographs of specimens frozen by the inventive method and comparing with prior art micro-photographs, such as those in the above-mentioned *Principles and Techniques in Diagnostic Histopathology* by Elias.

It is preferred that the submerging of the assembly in the pre-cooled fluorinated carbon fluid to freeze the assembly should be for about 0.5 to about 2 minutes, more preferably for about 0.7 minutes to about 1.5 minutes, and most preferably for about 1 minute.

Also, the submerging of the assembly in the pre-cooled fluorinated carbon fluid to freeze the assembly should be at a temperature of about −60° C. or lower. Such cold temperatures allow for the freezing procedure to be sufficiently rapid to avoid the formation of large ice crystals that destroy and/or distort anatomical structures, whereby specimen integrity is maintained. Preferably, the submerging of the assembly is at a temperature of about −70° C. or lower, and more preferably at a temperature of about −80° C. Although temperatures lower than about −80° C. can be employed, such cold temperatures are not desirable as they create a danger of the matrix/ specimen block cracking, so that it has to be removed and replaced in the solution to avoid this as a cracked specimen would destroy some of the structure, and make sectioning very difficult.

Additionally, instead of pre-cooling the container of fluorinated carbon fluid as described in the examples below, the pre-cooling to the desired temperature may be accomplished by various alternative ways, including, but not limited to, the following ways.

A first way is that the container of fluid may be placed directly in the bath bowl of a HISTOBATH™ (sometimes spelled HISTO BATH™, a refrigerated, recirculating unit available from Shandon of Pittsburgh, Pa.) at the desired temperature. Secondly, the container of fluid may be cooled in a Dewars flask (a thermos-like bottle) containing liquid nitrogen, while either stirring the fluid to keep it at the desired temperature or removing the container right at the desired temperature. Last, the container of fluid may be cooled directly by surrounding the sides and bottom thereof with a jacket of dry ice as with Algen's cryo prep, a commercially available "thermos-like" container that is charged with $CO_2$ to form a dry ice jacket.

By the phrase "hazard-free" as used herein with regard to the inventive method, is meant that the inventive method is accomplished with a fluid that is nontoxic to humans and/or free of adverse health effects to humans, and in particular that the fluid is practically non-toxic from inhalation of vapors or from ingestion by humans. Preferably, by "hazard-free" is also meant that the method is accomplished with a fluid that is also nonflammable, whereby the method is free of the hazard of fire/explosion. More preferably, by "hazard-free", is also meant that the method is accomplished with a fluid that also has an ODP=0, whereby the method is environmentally safe in that it is free of detrimental effects on the earth's protective ozone layer.

Therefore, the fluorinated carbon fluid employed in the inventive method, in addition to being non-toxic, preferably is non-flammable, whereby the method is free of fire/explosion hazards. More preferably, the fluorinated carbon fluid also has an ODP=0, whereby the method is environmentally safe in that the method is free of adverse effects on the protective ozone layer of the earth.

Also preferably, the fluorinated carbon compound employed as the fluid is a perfluorocarbon fluid, and most preferably is a perfluorocarbon fluid available from 3M Industrial Chemical Products Division, St. Paul, Minn., under the trade name PF–5060, the empirical formula of which is $C_6F_{14}$. 3M sells PF–5060 and other perfluorocarbon materials under the trade name, Fluorinert™ Electronic Liquids, for use in degreasing and liquid burn-in testing of electronic components, as described in 3M's sales brochures entitled "Advance Vapor Degreasing" (Dec., 1992) and "Liquid Burn-In Testing with Fluorinert™ Electronic Liquids" (Apr., 1993). Additionally, 3M sales personnel have indicated that some Fluorinert™ Electronic Liquids are useful as thermal shock fluid or for particle removal from microchips.

These brochures list several properties of the various perfluorocarbons being marketed by 3M, and indicated therein is that PF–5060 has an ODP=0, an average molecular weight=338, a boiling point=56° C., and a density=1.68 g/ml at 25° C. Also, as the material has no flash point, it is non-flammable.

In the examples below of the inventive method, the fluid employed for freezing the specimens in the freezing bath was $C_6F_{14}$ (PF–5060 from 3M). This material was found to be a suitable fluid for freezing specimens as it stays in the liquid state at temperatures of −60° C. to −80° C., or lower. Also importantly, at tissue freezing temperatures, PF–5060 does not extract either lipids or aqueous components from the samples as do some of the solvents it replaces.

LABORATORY EXAMPLES

The kidney and liver were excised from a sacrificial normal mouse and both were divided into portions. Then, selected kidney specimens and liver specimens were frozen according to the inventive method in $C_6F_{14}$ fluid (PF–5060 from 3M) as follows, and for comparison, as described further below, other selected kidney specimens and liver specimens were instead frozen directly in the cryostat without any $C_6F_{14}$ or other fluid.

For the inventive method, each specimen was placed within a cryo-mold that had been filled with a matrix (OCT gel comprised primarily of polyethylene glycol and resins, available from Miles Laboratories of Elkhart, Ind.) and thoroughly coated therewith. As the OCT gel surrounded the tissue specimens, it prevented them from freeze drying and enabled them to be manipulated during cryotomy without damage. The specimens were positioned inside the respective molds so that the anatomical structures of interest were on the bottom of the molds. Then, a small square of plastic film (vinylidene chloride copolymer film available under the trademark SARAN® from Dow of Midland, Mich.) was used to cover the surface of the tissue-containing, matrix-filled molds.

A resultant assembly with kidney tissue and a resultant assembly with liver tissue were then placed on the lower platform of a BEAKER BUDDY™ (a rack device, commercially available from U.S.A. Scientific of Ocala, Fla. or from Miles Laboratories of Elkhart, Ind.) and the cover of the BEAKER BUDDY fastened down. The platform has enough room for several molds. The BEAKER BUDDY, now holding the specimens to be frozen, was then plunged to the bottom of a steel container of $C_6F_{14}$ fluid that had already been pre-cooled to −78° C. The steel container of $C_6F_{14}$ fluid had been pre-cooled to the desired temperature by placing it within an ultra low temperature freezer at the desired temperature, and when cooled to that temperature, then removing the container and surrounding the sides and bottom thereof with an insulating jacket, i.e. a foamed polystyrene box set on a laboratory bench, to maintain the desired temperature during the tissue-freezing procedure.

While in the chilled fluid, each mold with tissue specimen froze in about 1 minute. Next, the BEAKER BUDDY with the frozen specimens thereon was removed from the $C_6F_{14}$, and the specimens taken from the BEAKER BUDDY and placed back into the ultra low freezer until sectioning could take place. The top of the fluid filled steel beaker was covered with aluminum foil and the beaker also returned to the ultra low freezer for future re-use.

Additionally, selected specimens were frozen in $C_6F_{14}$ fluid by using a ring of Tygon tubing to form a well around the cryostat chuck and inserting the chuck stem into one of the bottom holes of the BEAKER BUDDY before screwing on the cover of the BEAKER BUDDY.

The frozen specimens were then sectioned as follows with the cryostat set at 15° C. for the kidney specimens and then at 17° C. for the liver specimens. In turn, each frozen specimen was mounted, using OCT as a glue, to the specimen holder (also known as the chuck) of the cryostat. The chuck now attached to the specimen was fastened onto the microtome of the cryostat. The microtome has a surgical quality blade, usually held in a horizontal position and perpendicular to the vertical stroke of the frozen tissue being sectioned. As the face of the frozen tissue passed in front of the blade, the frozen tissue was cut into slices, called sections, of about 5 micrometers each in thickness.

Next, the sections were mounted on slides as follows. Each section was manipulated onto the flat, cold surface of the microtome blade with the aid of a fine, water-color brush. With the brush, the section was pulled by the edge provided by the OCT gel. Once the section was on the blade, a room temperature glass microscope slide was held over the still frozen section. The temperature differential between the frozen section and the comparatively warmer slide coming near it caused the section to jump onto the slide. The slide now containing the tissue section was then fixed with formalin and stained with an appropriate dye for the tissue to reveal its anatomical details.

The slides with the tissue sections were then examined using light microscopy to view the tissue morphology (anatomical details) at 10X, 20X and 40X.

For the comparison specimens, these were coated with the OCT gel in a mold and then wrapped in plastic film in the same manner as described above. However, instead of freezing with $C_6F_{14}$ fluid, a resultant assembly with kidney tissue and a resultant assembly with liver tissue were then placed directly into the chamber of the cryostat set at −25° C. and frozen in 5 minutes. The frozen comparison specimens were then sectioned in the cryostat, mounted on slides, et cetera, and viewed with light microscopy, in the same manner as described above for the inventive method wherein the specimens were frozen with $C_6F_{14}$ fluid cooled to −78° C.

The following are noted with regard to the inventive method of freezing and the samples that were frozen thereby.

First, and most important, the morphology of the specimens frozen in PF-5060 was comparable to that of specimens frozen in isopentane, and was better than that of the comparison specimens frozen directly in the cryostat without any PF-5060. No large ice crystals formed in the samples when PF-5060 was used for freezing.

It is imperative that in order to interpret frozen biological histology samples by light microscopy correctly, the tissue samples must be frozen correctly at ultra low temperatures so that anatomical details are not destroyed by the formation of large ice crystals. This task was accomplished with PF-5060. The prior fluids that could accomplish this task are either (1) isopentane, hexane, and acetone, which are toxic, hazardous, and flammable, and, because of these properties, difficult to store and dispose of and also subject to many Environmental Protection Agency regulations regarding use, or (2) FREON 12, which has been reported to be toxic (cause palpitations) to humans and is being phased out by recent regulations of the Environmental Protection Agency as it is known to be detrimental to the earth's ozone layer.

As compared to the prior art fluids, PF-5060 is nonflammable, non-toxic, not difficult to store and dispose of, and has an ODP=0. Thus, it does not present a danger to the laboratory technician of explosion/fire or of toxicity, and moreover, it is environmentally friendly to the earth's ozone layer.

It is additionally noted that evaporation of PF-5060 at low temperatures of −50° C. or lower was virtually nil, and thus little or no fluid was lost to the atmosphere during the freezing process.

Furthermore, it is noted that water has a very low solubility of 10 ppm at 25° C. in PF-5060, and thus during the freezing process, water condensed and formed a slurry on the surface of the fluid. The slurry was then was aspirated off and disposed of. In comparison, prior art fluids, such as acetone, are miscible with water and therefore water contaminates the fluid and compromises the cutting characteristics of the cryotomy matrix. Hence, the same aliquot of PF-5060 may be continually used in the freezing of specimens, and the small amounts of the fluid that are wasted as the specimen is removed from the fluid may be replenished by topping off.

Moreover, it is noted that with PF-5060, the cryotomy temperature may be brought to extremely low temperatures. However, as noted above, PF-5060 is very dense, having a density of 1.68 at 25° C. Therefore, at such low temperatures, the PF-5060 becomes very viscous and a magnetic stirring device with a magnetic stirring rod in the bath bowl could be employed in conjunction with the chilling bath in order to keep the fluid moving during the freezing of the specimen. However, this is unnecessary at temperatures down to −70C. or −80° C.

It will be understood that various details of the invention may be changed without further departing from the scope of the invention. Furthermore, the foregoing description is for the purpose of illustration only, and not for the purpose of limitation - the invention being defined by the claims.

What is claimed is:

1. A hazard-free method of freezing biological specimens to prepare them for examination by light microscopy, the method comprising:

(a) removing a biological specimen from a biological subject, wherein the biological specimen is selected from the group consisting of human tissue, animal tissue, and plant tissue;

(b) coating the specimen with a matrix by placing the specimen within a mold containing the matrix, whereby an assembly of mold with coated specimen therein is formed;

(c) freeze quenching the assembly to create a frozen assembly of frozen mold with frozen coated specimen therein and maintaining integrity of the frozen specimen, by submerging the assembly in a fluorinated carbon fluid that is non-toxic to humans and maintaining the assembly submerged therein for a time of about 0.5 to about 2 minutes sufficient to freeze the assembly, the fluid being
  (i) suitable for freezing specimens at temperatures of about −60° C. or lower,
  (ii) contained in an open receptacle,
  (iii) pre-cooled to a temperature of about −60° C. or lower, and
  (iv) a liquid when at ambient conditions of room temperature and pressure; and
(d) removing the frozen assembly of frozen mold with frozen coated specimen therein from the fluid.

2. The method of claim 1, wherein the pre-cooled temperature is about −70° C. or lower.

3. The method of claim 1, wherein maintaining the assembly submerged is accomplished with the fluorinated carbon fluid also being non-flammable.

4. The method of claim 1, wherein maintaining the assembly submerged is accomplished with the fluorinated carbon fluid also having an ozone depletion potential of 0, whereby said method is environmentally safe in that said method is free of adverse effects on the protective ozone layer of the earth.

5. The method of claim 1, wherein the freezing is accomplished with the fluorinated carbon fluid being a perfluorocarbon.

6. The method of claim 1, wherein the freezing is accomplished with the fluorinated carbon fluid being $C_6F_{14}$.

7. The method of claim 1, further including:
  (e) slicing the frozen assembly into sections with a cryostat;
  (f) mounting one or more of the sections on a slide or slides;
  (g) staining the one or more sections with a dye appropriate therefor; and
  (h) examining the one or more stained sections with a light microscope.

8. The method of claim 7, further including, after step (d) and prior to step (e): storing the frozen assembly in a cold atmosphere.

9. The method of claim 8, wherein storing the frozen assembly in a cold atmosphere is at an ultra low temperature of about −60° C. or lower.

10. The method of claim 7, further including, after step (f) and prior to step (g): storing the sections in a cold atmosphere.

11. The method of claim 10, wherein storing the sections in a cold atmosphere is at an ultra low temperature of about −60° C. or lower.

* * * * *